United States Patent [19]
Krepski et al.

[11] Patent Number: 5,492,805
[45] Date of Patent: Feb. 20, 1996

[54] BLOCKED LEUCO DYES FOR PHOTOTHERMOGRAPHIC ELEMENTS

[75] Inventors: Larry R. Krepski, White Bear Lake; Sharon M. Simpson; Kim M. Vogel, both of Lake Elmo, all of Minn.

[73] Assignee: Minnesota Mining and Manufacturing Company, St. Paul, Minn.

[21] Appl. No.: 269,438

[22] Filed: Jun. 30, 1994

[51] Int. Cl.$^6$ .................................................. G03C 1/498
[52] U.S. Cl. ...................... 430/619; 430/201; 430/203; 430/211; 430/256; 430/348; 430/955
[58] Field of Search ................................... 430/619, 955, 430/203, 211, 224, 223, 201, 256, 348

[56] References Cited

U.S. PATENT DOCUMENTS

| | | |
|---|---|---|
| 1,623,499 | 4/1927 | Sheppard et al. . |
| 2,131,038 | 9/1938 | Brooker et al. . |
| 2,274,782 | 3/1942 | Gaspar . |
| 2,399,083 | 4/1946 | Waller et al. . |
| 2,410,644 | 11/1946 | Flerke et al. . |
| 2,444,605 | 7/1948 | Heimbach et al. . |
| 2,489,341 | 11/1949 | Waller et al. . |
| 2,527,583 | 10/1950 | Silberstein et al. . |
| 2,565,418 | 8/1951 | Yackel et al. . |
| 2,566,263 | 8/1951 | Trivelli et al. . |
| 2,588,765 | 3/1952 | Robijns et al. . |
| 2,597,915 | 5/1952 | Yutzy et al. . |
| 2,614,928 | 10/1952 | Yutzy et al. . |
| 2,618,556 | 11/1952 | Hewitson et al. . |
| 2,681,294 | 6/1954 | Beguin . |
| 2,694,716 | 11/1954 | Allen et al. . |
| 2,701,245 | 2/1955 | Lynn . |
| 2,728,663 | 12/1955 | Allen et al. . |
| 2,761,791 | 9/1956 | Russell . |
| 2,839,405 | 6/1958 | Jones . |
| 2,886,437 | 5/1959 | Piper . |
| 2,956,879 | 10/1960 | Van Campen . |
| 2,960,404 | 11/1960 | Milton et al. . |
| 2,992,101 | 7/1961 | Jelley et al. . |
| 3,080,254 | 3/1963 | Grant, Jr. . |
| 3,121,060 | 2/1964 | Duane . |
| 3,180,731 | 4/1965 | Roman et al. . |
| 3,206,312 | 9/1965 | Sterman et al. . |
| 3,220,839 | 11/1965 | Herz et al. . |
| 3,220,846 | 11/1965 | Tinker et al. . |
| 3,241,969 | 3/1966 | Hart et al. . |
| 3,253,921 | 5/1966 | Sawdey . |
| 3,282,699 | 11/1966 | Jones et al. . |
| 3,287,135 | 11/1966 | Anderson et al. . |
| 3,297,446 | 1/1967 | Dunn . |
| 3,297,447 | 1/1967 | McVeigh . |
| 3,330,663 | 7/1967 | Weyde et al. . |
| 3,428,451 | 2/1969 | Trevoy . |
| 3,432,300 | 3/1969 | Lestina et al. . |
| 3,457,075 | 7/1969 | Morgan et al. . |
| 3,506,444 | 4/1970 | Haist et al. . |
| 3,531,286 | 9/1970 | Renfrew . |
| 3,573,050 | 3/1971 | Brannock et al. . |
| 3,574,627 | 4/1971 | Stern et al. . |
| 3,698,909 | 10/1972 | Lestina et al. . |
| 3,700,458 | 10/1972 | Lindholm . |
| 3,719,495 | 3/1973 | Lea . |
| 3,761,270 | 9/1973 | deMauriac et al. . |
| 3,764,337 | 10/1973 | Arai et al. . |
| 3,785,830 | 1/1974 | Sullivan et al. . |
| 3,839,049 | 10/1974 | Simons . |
| 3,847,612 | 11/1974 | Winslow . |
| 3,880,658 | 4/1975 | Lestina et al. . |
| 3,985,565 | 10/1976 | Gabrielsen et al. . |
| 4,021,240 | 5/1977 | Cerquone et al. . |
| 4,021,250 | 5/1977 | Sashihara et al. . |
| 4,022,617 | 5/1977 | McGuckin . |
| 4,042,394 | 8/1977 | Smith, Jr. et al. . |
| 4,055,428 | 10/1977 | Koyama et al. . |
| 4,060,420 | 11/1977 | Merkel et al. . |
| 4,076,539 | 2/1978 | Ikenoue et al. . |
| 4,088,496 | 5/1978 | Merkel . |
| 4,123,274 | 10/1978 | Knight et al. . |
| 4,123,282 | 10/1978 | Winslow . |

(List continued on next page.)

FOREIGN PATENT DOCUMENTS

| | | |
|---|---|---|
| 35262 | 9/1981 | European Pat. Off. . |
| 244399 | 5/1990 | European Pat. Off. . |
| 49-13224 | 2/1974 | Japan . |
| 50-17216 | 6/1975 | Japan . |
| 50-32928 | 10/1975 | Japan . |
| 51-42529 | 11/1976 | Japan . |
| 623448 | 5/1949 | United Kingdom . |
| 837095 | 6/1960 | United Kingdom . |
| 955061 | 4/1964 | United Kingdom . |
| 998949 | 7/1965 | United Kingdom . |
| 1326889 | 8/1973 | United Kingdom . |
| 1417586 | 12/1975 | United Kingdom . |
| 2100016 | 12/1982 | United Kingdom . |
| 90/00978 | 2/1990 | WIPO . |

OTHER PUBLICATIONS

J. Bailey et al., "The Photographic Color Development Process" in *The Chemistry of Synthetic Dyes;* K. Venkataraman, Ed.; *Academic Press:* New York; vol. IV, Chapter VI, 341–387 (1971).

(List continued on next page.)

*Primary Examiner*—Thorl Chea
*Attorney, Agent, or Firm*—Gary L. Griswold; Walter N. Kirn; Gregory A. Evearitt

[57] ABSTRACT

A photothermographic element containing a support bearing at least one heat-developable, photosensitive, image-forming photothermographic emulsion layer is provided. The emulsion layer comprises:

(a) a photosensitive silver halide;
(b) a non-photosensitive, reducible source of silver;
(c) a leuco dye reducing agent; and
(d) a binder;

wherein the leuco dye reducing agent comprises a blocked leuco dye compound of the general formula L-R$^1$, which is capable of being oxidized to a colored form, wherein:

(i) L is a group remaining after removal of a hydrogen from a leuco dye; and
(ii) R$^1$ is a C(O)—NH—SO$_2$—R$^5$ group wherein R$^5$ is an aliphatic group or an aromatic group.

18 Claims, No Drawings

U.S. PATENT DOCUMENTS

| | | |
|---|---|---|
| 4,187,108 | 2/1980 | Willis. |
| 4,220,709 | 9/1980 | deMauriac. |
| 4,260,677 | 4/1981 | Winslow et al.. |
| 4,336,322 | 6/1982 | Fujita et al.. |
| 4,368,247 | 1/1983 | Fletcher, Jr. et al.. |
| 4,374,921 | 2/1983 | Frenchik. |
| 4,426,441 | 1/1984 | Adin et al.. |
| 4,455,363 | 6/1984 | Naito et al.. |
| 4,460,681 | 7/1984 | Frenchik. |
| 4,463,079 | 7/1984 | Naito et al.. |
| 4,469,773 | 9/1984 | Adin et al.. |
| 4,473,631 | 9/1984 | Hirai et al.. |
| 4,474,857 | 10/1984 | Vaughn, Jr.. |
| 4,474,867 | 10/1984 | Naito et al.. |
| 4,499,180 | 2/1985 | Hirai et al.. |
| 4,511,650 | 4/1985 | Hirai et al.. |
| 4,563,415 | 1/1986 | Brown et al.. |
| 4,594,307 | 6/1986 | Ishida. |
| 4,619,892 | 10/1986 | Simpson et al.. |
| 4,622,395 | 11/1986 | Bellus et al.. |
| 4,656,124 | 4/1987 | Komamura. |
| 4,670,374 | 6/1987 | Bellus et al.. |
| 4,708,928 | 11/1987 | Geisler. |
| 4,710,570 | 12/1987 | Thien. |
| 4,731,321 | 3/1988 | Sato et al.. |
| 4,761,361 | 8/1988 | Ozaki et al.. |
| 4,775,613 | 10/1988 | Hirai et al.. |
| 4,782,010 | 11/1988 | Mader et al.. |
| 4,883,747 | 11/1989 | Grieve et al.. |
| 4,889,932 | 12/1989 | Miller. |
| 4,923,792 | 5/1990 | Grieve et al.. |
| 4,981,775 | 1/1991 | Swain et al.. |
| 5,023,229 | 6/1991 | Evans et al.. |
| 5,064,742 | 11/1991 | Aono et al.. |
| 5,262,272 | 11/1993 | Eian et al.. |
| 5,266,452 | 11/1993 | Kitchin et al.. |
| 5,330,864 | 7/1994 | Biavasco et al.. |

OTHER PUBLICATIONS

E. Brinckman et al., "Reduction of a sensitized silver soap" in *Unconventional Imaging Processes;* Focal Press: London; pp. 74–75; 1978.

G. H. Brown et al., "Azomethine Dyes. II. Color and Constitution of Acylacetamide Azomethine Dyes", *Color and Constitution of Acylacetamide Azomethine Dyes*, 79, 2919–2927 (Jun. 5, 1957).

"Carbamoyloxy substituted couplers in a photothermographic element and process", *Research Disclosure,* No. 23419, pp. 314–315, Oct. 1983.

J. W. Carpenter et al., "Photothermographic silver halide systems", *Research Disclosure,* No. 17029, pp. 9–15, Jun. 1978.

D. R. Cassady et al., "Sulfonylureas and Related Compounds", *J. Org. Chem.*, 23, 923–926 (Jun. 1958).

L. J. Fleckenstein, "Color Forming Agents" in *The Theory of the Photographic Process;* T. H. James et al. (Eds.); Macmillan Publishing Co. Inc.: New York, N.Y.; Fourth Edition, 353–354 (1977).

J. M. Harbison et al., "Chemical Sensitization and Environmental Effect", in *The Theory of the Photographic Process;* T. H. James et al. (Eds.); Macmillian Publishing Co., Inc.: New York, N.Y.; Fourth Edition, Chapter 5, 149–169 (1977).

J. P. Kitchin et al., "Hydazine–Promoted Infectious Development of Silver Halide—An Improved Process", *J. Imag. Tech.*, 15, 282–284 (Dec. 1989).

D. H. Klosterboer, "Thermally Processed Silver Systems" in *Imaging Processes and Materials,* Neblettes Eighth Edition; J. Sturge et al. (Eds.); Van Nostrand Reinhold: New York; Chapter 9, 279–291 (1989).

P. W. Lauf, "Photothermographic Silver Halide Systems", *Research Disclosure,* No. 29963, pp. 208–214, Mar. 1989.

"Methine and Polymethine Colouring Matters" in *The Colour Index;* The Society of Dyes and Colourists: Yorkshire, England; 4, 4437 (1971).

"Photothermographic silver halide material and process", *Research Disclosure,* No. 22812, pp. 155–156, Apr. 1983.

D. J. Savage, "Synthesis and Polymerization of Dimethylaminophenyl Isocyanates" *Polymer Letters,* 12, 529–533 (1974).

G. L. Stahl et al., "General Procedure for the Synthesis of Mono–N–acylated 1,6–Diaminohexanes", *J. Org. Chem,* 43, 2285–2286 (1978).

H. Ulrich et al., *Agnew. Chem., Int. Ed.*, 5, 704–712 (1966).

BLOCKED LEUCO DYES FOR PHOTOTHERMOGRAPHIC ELEMENTS

BACKGROUND OF THE INVENTION

1. Field of the Invention:

This invention relates to leuco dyes. More specifically, this invention relates to novel blocking groups for the preparation of blocked leuco dyes, particularly cyan, magenta, and yellow blocked chromogenic leuco dyes, that are suitable for use in photothermographic imaging systems.

2. Background Art:

Silver halide-containing, photothermographic imaging materials (i.e., heat-developable photographic elements) processed with heat, and without liquid development, have been known in the art for many years. These materials, also known as "dry silver" compositions or emulsions, generally comprise a support having coated thereon: (a) a photosensitive material that generates elemental silver when irradiated; (b) a non-photosensitive, reducible silver source; (c) a reducing agent for the non-photosensitive, reducible silver source; and (d) a binder. The photosensitive material is generally photographic silver halide that must be in catalytic proximity to the non-photosensitive, reducible silver source. Catalytic proximity requires an intimate physical association of these two materials so that when silver specks or nuclei are generated by irradiation or light exposure of the photographic silver halide, those nuclei are able to catalyze the reduction of the reducible silver source. It has long been understood that elemental silver ($Ag^{\circ}$) is a catalyst for the reduction of silver ions, and that the photosensitive silver halide can be placed into catalytic proximity with the non-photosensitive, reducible silver source in a number of different fashions. For example, catalytic proximity can be accomplished by partial metathesis of the reducible silver source with a halogen-containing source (see, for example, U.S. Pat. No. 3,457,075); by coprecipitation of silver halide and the reducible silver source material (see, for example, U.S. Pat. No. 3,839,049); and other methods that intimately associate the photosensitive photographic silver halide and the non-photosensitive, reducible silver source.

The non-photosensitive, reducible silver source is a material that contains silver ions. Typically, the preferred non-photosensitive reducible silver source is a silver salt of a long chain aliphatic carboxylic acid having from 10 to 30 carbon atoms. The silver salt of behenic acid or mixtures of acids of similar molecular weight are generally used. Salts of other organic acids or other organic materials, such as silver imidazolates, have been proposed. U.S. Pat. No. 4,260,677 discloses the use of complexes of inorganic or organic silver salts as non-photosensitive, reducible silver sources.

In both photographic and photothermographic emulsions, exposure of the photographic silver halide to light produces small clusters of silver atoms ($Ag^{\circ}$). The imagewise distribution of these clusters is known in the art as a latent image. This latent image is generally not visible by ordinary means. Thus, the photosensitive emulsion must be further processed in order to produce a visible image. The visible image is produced by the reduction of silver ions, which are in catalytic proximity to silver halide grains bearing the clusters of silver atoms, i.e., the latent image. This produces a black and white image.

As the visible image is produced entirely by elemental silver ($Ag^{\circ}$), one cannot readily decrease the amount of silver in the emulsion without reducing the maximum image density. However, reduction of the amount of silver is often desirable in order to reduce the cost of raw materials used in the emulsion. One method of attempting to increase the maximum image density in photographic and photothermographic emulsions without increasing the amount of silver in the emulsion layer is by incorporating dye-forming materials in the emulsion and producing color images.

A number of methods have been proposed for obtaining color images with dry silver systems. Such methods include, for example, incorporating dye-forming coupler materials into the dry silver systems. For example, known color-forming dry silver systems include: a combination of silver benzotriazole, a magenta, yellow or cyan dye-forming coupler, an aminophenol developing agent, a base release agent such as guanidinium trichloroacetate, and silver bromide in poly(vinyl butyral); and a combination of silver bromoiodide, sulphonamidophenol reducing agent, silver behenate, poly(vinyl butyral), an amine such as n-octadecylamine, and 2-equivalent or 4-equivalent cyan, magenta or yellow dye-forming couplers.

Color images can also be formed by incorporation of leuco dyes into the emulsion. A leuco dye is the reduced form of a color-bearing dye. It is generally colorless or very lightly colored. Upon imaging, the leuco dye is oxidized, and the color-bearing dye and a reduced silver image are simultaneously formed in the exposed region. In this way, a dye enhanced silver image can be produced, as shown, for example, in U.S. Pat. Nos. 4,187,108; 4,374,921; and 4,460,681.

Multicolor photothermographic imaging elements typically comprise two or more monocolor-forming emulsion layers (often each emulsion layer comprises a set of bilayers containing the color-forming reactants) maintained distinct from each other by barrier layers. The barrier layer overlaying one photosensitive, photothermographic emulsion layer typically is insoluble in the solvent of the next photosensitive, photothermographic emulsion layer. Photothermographic elements having at least two or three distinct color-forming emulsion layers are disclosed in U.S. Pat. Nos. 4,021,240 and 4,460,681. Various methods to produce dye images and multicolor images with photographic color couplers and leuco dyes are well know in the art as represented by U.S. Pat. Nos. 4,022,617; 3,531,286; 3,180,731; 3,761,270; 4,460,681; 4,883,747; and *Research Disclosure*, March 1989, item 29963.

When the reactants and reaction products of photothermographic systems remain in contact after imaging, several problems can result. A common problem is the instability of the image following processing. The photoactive silver halide still present in the developed image can continue to catalyze development of metallic silver even under room light, thereby causing a strong increase of fog after development. This development of fog is also increased by exposure to oxygen, which causes the oxidation of leuco dyes. For example, U.S. Pat. Nos. 4,670,374 and 4,889,932 describe photothermographic materials containing oxidizable leuco phenazine, phenoxazine, or phenothiazine dyes useful for color photothermographic images, which are subject to air oxidation causing fog after development. In addition, for photothermographic systems containing leuco dyes the resulting prints tend to develop color in unimaged background areas during storage. This "background stain" is caused by slow reaction between the leuco dye and an oxidizing agent.

Another problem for photothermographic systems containing leuco dyes is the lack of stability of the leuco dye before exposure. In fact, in many cases, it is not possible to obtain any images because the leuco dye reacts in a non-imagewise manner before exposure. The consequence of this non-imagewise reaction is the absence of differences in density between the imaged and non-imaged areas. This means that there is no difference in the development between the parts that should have produced an image and the parts that should not have produced an image.

Thus, there exists a need for useful leuco dyes for photothermographic materials that are stable enough not to be oxidized by contact with air or by simple heating, and which limit fog formation after development. One approach by which these criteria can be met is through the use of blocking or modifying groups that assist in providing stability to the leuco dyes and in decreasing their diffusibility. The blocking groups must also be easily removed from the leuco dye during processing without the use of highly basic solutions or other reagents that cause adverse effects on the other components of the imaging construction. Furthermore, the blocked leuco dyes must react imagewise to provide a good dye image.

British Patent No. GB 1,417,586 describes oxichromic compounds containing a reduced azomethine linkage that can be blocked with a group that prevents oxidation of the nitrogen atom of the azomethine linkage. Such compounds produce a chromophore useful in color photographic systems in silver halide transfer materials upon chromogenic oxidation and upon removal of the blocking group by hydrolysis in alkaline solution. European Patent Application No. 35,262, and PCT Patent Application No. WO 90-00978 describe, respectively, non-silver copy materials and non-silver heat-sensitive materials both having leuco dyes with the same —$SO_2$— protecting group. These leuco dyes are useful in heat-sensitive materials; however, they are not useful in photothermographic materials because they do not react imagewise to give a dye image. In fact, when the material containing such leuco dyes is exposed and developed according to the usual process for photothermographic materials, it does not present any difference in density between the imaged and non-imaged areas.

There are relatively few blocking groups that can be used to stabilize leuco dyes, particularly chromogenic leuco dyes, in photothermographic materials. A few examples include —C(O)—NH—$C_6H_4$—N($CH_3$)$_2$, —C(O)—NH—$C_6H_4$—N($CH_2CH_3$)$_2$, —C(O)—NH—($CH_2$)$_3$—$CH_3$, —C(O)—NH—$CH_2$—CH=$CH_2$, —C(O)—$C_5H_{11}$, —C(O)—$OC_3H_7$, —C(O)—NH—$C_6H_4$—$CH_3$, —C(O)—NH—$C_2H_5$, —C(O)—NH—$C_6H_5$, —C(O)—NH—$C_3H_7$, —C(O)—$C_6H_5$, —C(O)—$C_6H_4$—OH. Also, chromogenic leuco dyes having various protecting groups such as carbamoyl are described in Applicants' Assignee's copending application Ser. Nos. 07/939,093 (filed Sep. 2, 1992 which issued as U.S. Pat. No. 5,330,864 on Jul. 19, 1994) and 08/161,900 (filed Dec. 3, 1993). Because of the limited number of blocking groups, there are limited numbers of photothermographic systems. Thus, a need exists for more leuco dye blocking groups, particularly blocking groups that are easy to remove during development and allow for the formation of sufficient differences in density between imaged and non-imaged areas.

SUMMARY OF THE INVENTION

The present invention provides blocked leuco dyes, preferably blocked chromogenic leuco dyes, and photothermographic elements containing these blocked leuco dyes that are capable of being oxidized to a colored form. The photothermographic elements of the present invention include a support bearing at least one heat-developable, photosensitive, image-forming photothermographic emulsion layer comprising:

(a) a photosensitive silver halide;
(b) a non-photosensitive, reducible source of silver;
(c) a leuco dye reducing agent; and
(d) a binder.

The leuco dye reducing agent is a blocked leuco dye compound of the general formula L-$R^1$ wherein: L is a group remaining after removal of a hydrogen from an unblocked leuco dye; and $R^1$ is the blocking group —C(O)—NH—$SO_2$—$R^5$ wherein $R^5$ is an aliphatic group (preferably containing 1–50 carbon atoms) or an aromatic group (preferably containing 5–50 carbon atoms). Within this definition of $R^5$ are included ballasting groups, such as high molecular weight hydrocarbon groups or polymeric groups (alternatively $R^5$ can be considered to be attached to a ballasting polymer). Certain preferred blocked leuco dyes include blocking groups in which $R^5$ is an alkyl group containing 1–20 carbon atoms or an aryl group containing 5–30 carbon atoms. Particularly preferred blocked leuco dyes include blocking groups in which $R^5$ is a substituted phenyl group, such as p-tolyl.

One class of preferred blocked leuco dyes of the present invention is the class of blocked chromogenic leuco dyes of the formula:

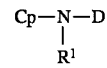

wherein: Cp is a coupler group, preferably a photographic coupler group; N-D is a photographic developer group, preferably a color photographic developer group; and $R^1$ is a —C(O)—NH—$SO_2$—$R^5$ group as described above. Of the blocked chromogenic leuco dyes, preferred dyes are represented by the general formula:

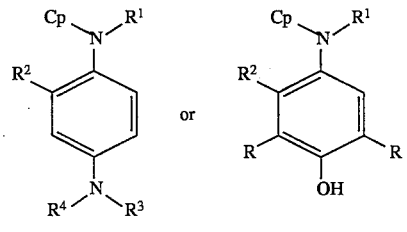

wherein: R is hydrogen or halogen; $R^1$ is a —C(O)—NH—$SO_2$—$R^5$ group, wherein $R^5$ is an aliphatic group (preferably containing 1–50 carbon atoms) or an aromatic group (preferably containing 5–50 carbon atoms); $R^2$ is a hydrogen atom, an alkoxy group (preferably containing 1–20 carbon atoms), or an alkyl group (preferably containing 1–20 carbon atoms); $R^3$ and $R^4$ are each independently an aliphatic group (preferably containing 1–50 carbon atoms), an aromatic group (preferably containing 5–30 carbon atoms), or an -X-Y group, wherein X is an alkylene group (preferably containing 1–4 carbon atoms), and Y is a cyano group, a halogen atom, an alkoxy group (preferably containing 1–20 carbon atoms), or —OH; and Cp is a coupler group (preferably a photographic coupler group). Preferred blocked chromogenic leuco dyes include blocking groups containing preferred $R^5$ groups as defined above; $R^2$ groups such as a hydrogen atom, an alkyl group containing 1–20 carbon atoms, or an alkoxy group containing 1–20 carbon atoms; and $R^3$ and $R^4$ groups such as an alkyl group containing 1–20 carbon atoms or an aromatic group containing 5–30 carbon atoms.

As is well understood in this technical area, a large degree of substitution is not only tolerated, but is often advisable. As a means of simplifying the discussion and recitation of certain terminology used throughout this application, the terms "group" and "moiety" are used to differentiate between chemical species that allow for substitution or which may be substituted and those which do not so allow or may not be so substituted. Thus, when the term "group" is used to describe a chemical substituent, the described chemical material includes the unsubstituted group and that group with conventional substitution. Where the term "moiety" is used to describe a chemical compound or substituent, only an unsubstituted chemical material is intended to be included. For example, the phrase "alkyl group" is intended to include not only pure open-chain and cyclic saturated hydrocarbon alkyl substituents, such as methyl, ethyl, propyl, t-butyl, cyclohexyl, adamantyl, octadecyl, and the like, but also alkyl substituents bearing further substituents known in the art, such as hydroxyl, alkoxy, vinyl, phenyl, halogen atoms (F, Cl, Br, and I), cyano, nitro, amino, carboxyl, etc. On the other hand, the phrase "alkyl moiety" is limited to the inclusion of only pure open-chain and cyclic saturated hydrocarbon alkyl substituents, such as methyl, ethyl, propyl, t-butyl, cyclohexyl, adamantyl, octadecyl, and the like.

As used herein, the term "emulsion layer" means a layer of a photothermographic element that contains a photosensitive silver salt and a non-photosensitive, reducible silver source. The term "change in color" includes an increase in optical density of at least 0.2 units between the unexposed and the exposed regions. The term "leuco dye" refers to the reduced form of a dye that is generally colorless or very lightly colored and is capable of forming a colored image upon oxidation of the leuco dye to the dye form. The term "chromogenic leuco dye" refers to a class of leuco dyes prepared by oxidative coupling of a p-phenylenediamine compound or a p-aminophenol compound with a coupler or reductive coupling of a chromogenic dye with a blocking group. For a review of chromogenic leuco dyes, see K. Venkataraman, *The Chemistry of Synthetic Dyes*; Academic Press: New York, 1952; Vol. 4, Chapter VI.

Other aspects, advantages, and benefits of the present invention are apparent from the detailed description, the examples, and the claims.

DETAILED DESCRIPTION OF THE INVENTION

As stated above, silver halide-containing photothermographic imaging materials, i.e., "dry silver" compositions or emulsions, generally include a support having coated thereon:

(a) a photosensitive material that generates elemental silver when irradiated, e.g., a photosensitive silver halide;

(b) a non-photosensitive, reducible source of silver;

(c) a reducing agent for the non-photosensitive, reducible silver source; and (d) a binder.

Specifically, the present invention is directed to such compositions containing a blocked leuco dye as the reducing agent, The blocked leuco dye reducing agents of the present invention include novel sulfonyl-containing amide blocking groups, i.e., $-C(O)-NH-SO_2-$ groups.

The Dye-Forming Material

The reducing agent for the reducible source of silver used in the present invention is a blocked leuco dye compound that can be oxidized to a colored form, i.e., the dye, by silver ion to form a visible image. It is to be understood, however, that blocked leuco dyes that are sensitive only to changes in pH (and are not oxidizable) are not included within the scope of leuco dyes useful in this invention because they are not oxidizable to a colored form. Preferred blocked leuco dyes are those that oxidize to a colored form when heated to a temperature of about 80°–250° C. (176°–482° F.) for a duration of about 0.5–300 seconds.

The blocked leuco dyes of the present invention are represented by the general formula $L-R^1$, wherein L represents a group remaining after removal of a hydrogen from an unblocked leuco dye and $R^1$ represents the sulfonyl-containing amide blocking group. The blocking group $R^1$ can be further represented by $-C(O)-NH-SO_2-R^5$ wherein $R^5$ represents an aliphatic group or an aromatic group, as described in further detail below in the discussion of preferred blocked chromogenic leuco dyes. As used herein, a "leuco dye," "unblocked leuco dye," or "blocked leuco dye" is the reduced form of a dye that is generally colorless or very lightly colored and is capable of forming a colored image upon oxidation of the leuco or blocked leuco dye to the dye form. Thus, the blocked leuco dyes, i.e., blocked dye-forming compounds, of the present invention absorb less strongly in the visible region of the electromagnetic spectrum than do the dyes, i.e., the oxidized form of the blocked leuco dyes. The resultant dye produces an image either directly on the sheet on which the dye is formed or, when used with a dye- or image-receiving layer, on the image-receiving layer upon diffusion through emulsion layers and interlayers.

Representative classes of leuco dyes that can be blocked with the sulfonyl-containing amide blocking groups of the present invention include, but are not limited to: indoaniline leuco dyes; imidazole leuco dyes, such as 2-(3,5-di-t-butyl-4-hydroxyphenyl)-4,5-diphenylimidazole, as described in U.S. Pat. No. 3,985,565; dyes having an azine, diazine, oxazine, or thiazine nucleus, such as those described in U.S. Pat. Nos. 4,563,415; 4,622,395; 4,710,570; and 4,782,010; and benzylidene leuco compounds as described in U.S. Pat. No. 4,923,792.

A particularly preferred class of leuco dyes useful in this invention are those derived from so-called "chromogenic leuco dyes." Chromogenic leuco dyes of this class can be prepared by reduction of the corresponding dye as described in U.S. Pat. No. 4,374,921, and as described later herein.

A particularly preferred class of chromogenic leuco dye reducing agents is represented by the following general formula:

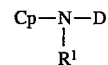

wherein: $R^1$ is a sulfonyl-containing amide blocking group, "Cp" is a photographic coupler group, preferably a photographic coupler group; and "N-D" is a photographic developer group, preferably a color photographic developer group, obtained from a developer, such as a primary aromatic amine color photographic developer. Typical couplers include phenolic derivatives and materials with an active methylene group. Typical developers include phenylenediamine and aminophenol derivatives.

The preferred blocked chromogenic leuco dyes of the present invention are represented by the general Formulae I or II:

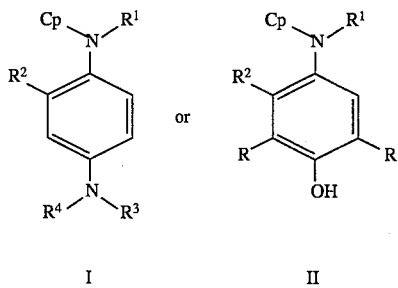

I  II wherein:

(a) R is hydrogen or halogen (preferably Cl);

(b) $R^1$ is a C(O)—NH—SO$_2$—$R^5$ group, wherein $R^5$ is an aliphatic group or an aromatic group;

(c) $R^2$ is a hydrogen atom, an alkoxy group, or an alkyl group;

(d) $R^3$ and $R^4$ are each independently an aliphatic group, an aromatic group, or an -X-Y group, wherein X is an alkylene group containing 1–carbon atoms, and Y is a cyano group, a halogen atom, an alkoxy group containing 1–20 carbon atoms, or —OH; and (e) Cp is a coupler group.

In the context of the present invention, the term "aliphatic" means a saturated or unsaturated linear, branched, or cyclic hydrocarbon group. This term is used to encompass alkyl and vinyl groups, for example. The term "alkyl" means a saturated linear, branched, or cyclic hydrocarbon group. The term "alkoxy" means an alkyl group attached to a molecule by oxygen. The terms "aromatic" or "aryl" mean a mono- or polynuclear aromatic hydrocarbon group, including alkaryl and aralkyl groups.

Yellow, magenta, and cyan forming blocked leuco dyes of Formulae I and II can be generally prepared by selecting the appropriate coupler and developer. The blocked leuco dyes of Formula I can be prepared as described below. Blocked leuco dyes of Formula II can be made by synthetic procedures that are substantially similar to those used for the preparation of blocked leuco dyes of Formula I.

In Formulae I and II, as well as all blocked leuco dyes described herein that contain the sulfonyl-containing amide blocking group of the formula —C(O)—NH—SO$_2$—$R^5$, $R^1$ is a —C(O)—NH—SO$_2$—$R^5$ group wherein $R^5$ is a linear, cyclic, or branched aliphatic group (preferably containing 1–50 carbon atoms) or an aromatic group (preferably containing 5–50 carbon atoms). Preferably $R^5$ is an alkyl group, linear, cyclic, or branched (preferably containing 1 to 20 carbon atoms and more preferably containing 1 to 8 carbon atoms), or an aromatic, i.e., aryl, group containing 5 to 30 carbon atoms. More, preferably, $R^5$ is a phenyl group, and most preferably, $R^5$ is a p-tolyl group.

Examples of suitable alkyl groups include methyl, ethyl, propyl, butyl, t-butyl, etc. Examples of suitable aryl groups include a phenyl group, e.g., a p-tolyl group or a p-methoxy phenyl group, a naphthyl group, or other aryl group of up to 30 carbon atoms. Included within the scope of the "aryl" or "aromatic" groups, as used herein, are groups containing both aromatic and aliphatic groups in the main chain, such as —CH$_2$—CH$_2$—C$_6$H$_4$—CH$_2$-CH$_2$—. Whether aliphatic or aromatic, the $R^5$ group is allowed to have a single substituent or a plurality of substituents, which may be the same or different, that do not react with an isocyanate. Examples include halogen atoms (such as fluorine, chlorine, bromine, etc.), alkyl groups (such as methyl, ethyl, propyl, butyl, dodecyl, etc.), aryl groups, ester groups, nitro groups, nitrile groups, alkoxy groups (such as methoxy, ethoxy, etc.), and the like.

It is to be understood that the aliphatic or aromatic $R^5$ group can be a ballasting group. As used herein, a "ballasting group" is an organic group that reduces the thermal mobility of the blocked chromogenic leuco dye in the binder and is capable of being oxidatively cleaved. The ballasting group is of a sufficient molecular weight to render the blocked leuco dye substantially thermally immobile at a temperature of about 80°–250° C. The molecular weight of the ballasting group must not be so high, however, that the resulting amount of the oxidized dye is insufficient to yield a dye image having a reflection optical density of at least 0.3 or a transmission optical density of at least 0.2. To meet these requirements, the ballasting group has a molecular weight of at least about 183 and no greater than about 20,000. Preferably, the ballasting group molecular weight is at least about 237 and no greater than about 15,000, more preferably at least about 337 and no greater than about 10,000, and most preferably at least about 337 and no greater than about 20,000. Representative examples of ballasting groups include long chain aliphatic groups, e.g., having at least 8 carbon atoms, aromatic rings containing a long chain aliphatic group, e.g., having at least 8 carbon atoms, preferably an aromatic ring containing a long chain alkoxy group, e.g., having at least 8 carbon atoms. Representative examples of ballasted blocking groups within the scope of $R^1$ used in the blocked leuco dyes of the present invention include: —C(O)—NH—SO$_2$—C$_6$H$_4$—O—C$_8$H$_{16}$—OH; —C(O)—NH—SO$_2$—C$_6$H$_4$—O—C$_{12}$H$_{25}$; —C(O)—NH—SO$_2$—C$_6$H$_4$—O—C$_{18}$H$_{37}$; —C(O)—NH—SO$_2$—C$_6$H$_4$—O—C$_{22}$H$_{45}$; and —C(O)—NH—SO$_2$—C$_6$H$_4$—O—C(O)—NH—(CH$_2$)$_{36}$—NH—C(O)—OCH$_3$.

It is also to be understood that the aliphatic or aromatic $R^5$ group can be attached to or incorporated within a polymer. Use of a polymer ballasting group is a particularly effective method of ballasting the blocked leuco dye, thus rendering the blocked leuco dye substantially thermally immobile at a temperature of about 80°–250° C., and thus providing differential mobility between the released dye and blocked leuco dye. The number of carbons in the polymer would not be included within the number of carbons in the $R^5$ group.

In Formulae I and II, $R^2$ can be a hydrogen atom, an alkoxy group, or an alkyl group. Preferably the alkoxy group contains 1–20 carbon atoms. Preferably the alkyl group contains 1–20 carbon atoms and more preferably 1–4 carbon atoms. Examples of suitable alkyl and alkoxy groups include methyl, methoxy, ethyl, ethoxy, propyl, propoxy, butyl, butoxy, and the like.

In Formulae I and II, $R^3$ and $R^4$ can be an aliphatic group, an aromatic group, or an -X-Y group as defined above. When Y is an —OH group, an excess of sulfonyl isocyanate may be needed if competitive reactions are a problem. Preferably, the aliphatic group contains 1–50 carbon atoms, more preferably 1–20 carbon atoms, and most preferably 1–4 carbon atoms. Of the aliphatic groups, alkyl groups are preferred. Preferably, the aromatic group contains 5–30 carbon atoms. More preferably, the aromatic group contains 5–14 carbon atoms, and most preferably 5–10 carbon atoms. As used herein, the term "aromatic" includes groups containing both aromatic and aliphatic groups in the main chain, such as —CH$_2$—C$_6$H$_4$—CH$_2$—. Whether aliphatic or aromatic, the $R^3$ and $R^4$ groups can have one or more substituents, which may be the same or different, that do not react with an isocyanate. Examples include halogen atoms, hydroxyl, and cyano groups.

Chromogenic dyes of Formulae I and II, as well as other leuco dyes containing the sulfonyl-containing amide blocking group, are advantageous at least because of the relatively high reactivity imparted by the electron withdrawing sulfonyl group ($-SO_2-$) to the blocking amide functionality ($-C(O)-NH-SO_2-R_5$), thereby allowing for relatively easy cleavage of the blocking group during development of the colored image. Also, the sulfonyl group enhances the reactivity of the starting sulfonyl isocyanate blocking reagent ($R^5-SO_2-NCO$) relative to an isocyanate without the sulfonyl group. This reactivity allows for forming blocked leuco dyes in situations where it would not be possible with an ordinary isocyanate. Information on the chemistry and preparation of sulfonyl isocyanate compounds is described in H. Ulrich et al., *Angew. Chem., Int. Ed.*, 5, 704 (1966); and D. R. Cassady et al., *J. Org. Chem.*, 23, 923 (1958).

Of the dyes of Formulae I and II, the more preferred dyes of the present invention are the compounds of Formula I. The most preferred blocked chromogenic leuco dyes are compounds; having Formula I wherein $R^5$ is a p-tolyl group.

As noted above, Cp is a coupler group. Couplers are materials that when reacted with an oxidized photographic developer (e.g., a p-phenylenediamine, a p-phenylenediamine or their derivatives) couple with the oxidized developer and form dyes. The "coupler group" is that portion of the coupler remaining after reaction with the oxidized developer. The coupler group, as compared to the coupler, will have the developer residue bonded to the coupler at a position on the coupler previously occupied by a hydrogen atom or other splitting-off group at the coupling position of the coupler.

Preferably, Cp is a photographic coupler group. The term "photographic coupler group" has an accepted meaning within the photographic art. Examples of photographic couplers useful in the present invention are described in T. H. James, *The Theory of the Photographic Process*, Fourth Edition, 1977, Macmillian, N.Y. Further examples of couplers useful in the present invention are disclosed in U.S. Pat. Nos. 4,426,441 and 4,469,773, incorporated herein by reference. Representative couplers are shown in Table I:

TABLE I

Representative Couplers

Magenta Couplers

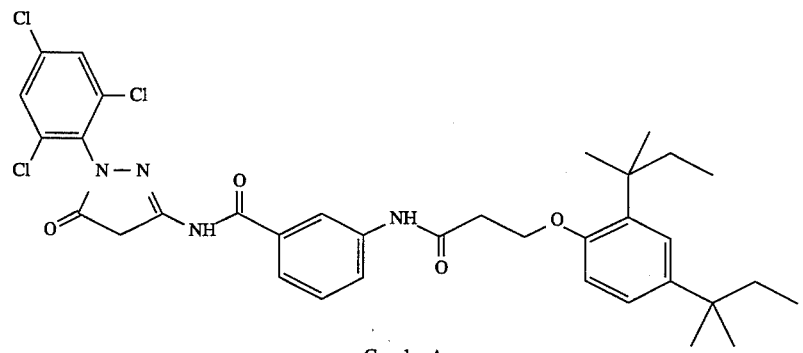

Coupler A

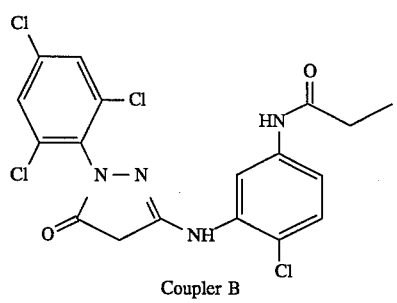

Coupler B

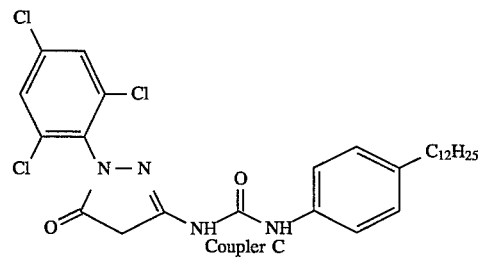

Coupler C

TABLE I-continued
Representative Couplers
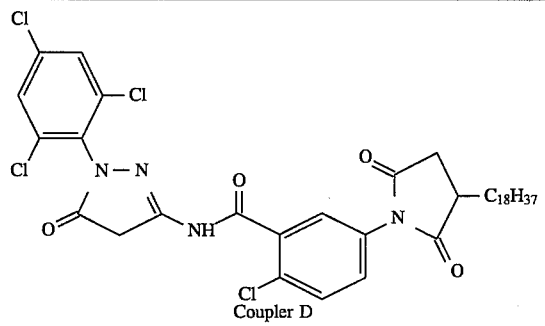
Coupler D
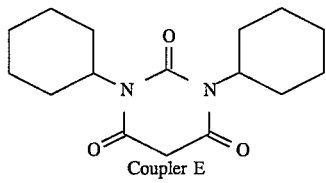
Coupler E
Yellow Couplers
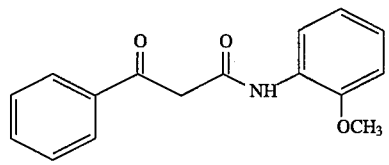
Coupler F
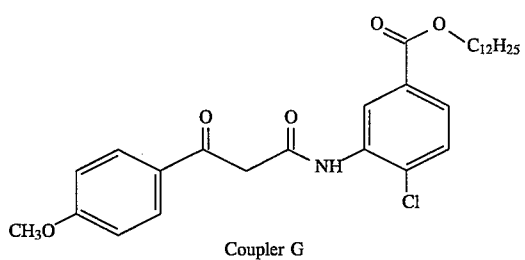
Coupler G
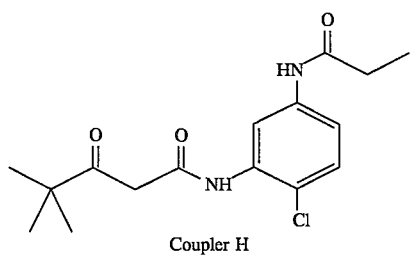
Coupler H
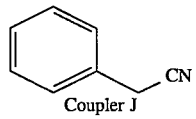
Coupler J

TABLE I-continued

Representative Couplers

Cyan Couplers

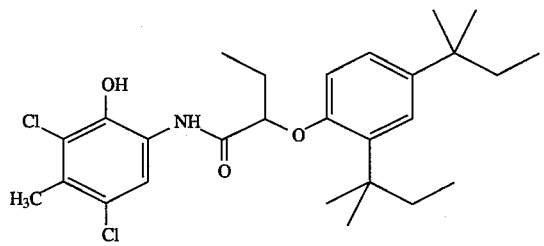

Coupler K

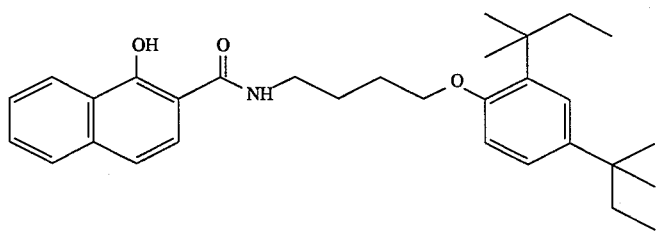

Coupler L

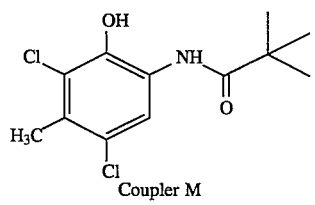

Coupler M

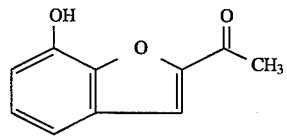

Coupler N

Examples of developers useful in the present invention are described in T. H. James, *The Theory of the Photographic Process*, Fourth Edition, 1977, Macmillan, N.Y.; Chapter 12, pages 353 to 354. Preferred developers are those derived from p-phenylenediamines and p-aminophenols. Representative developers are shown in Table II.

TABLE II

Representative Developers

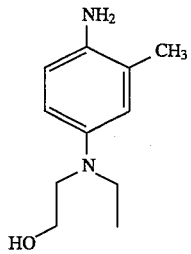

Developer A

TABLE II-continued

Representative Developers

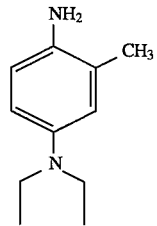

Developer B

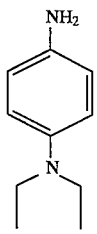

Developer C

TABLE II-continued

Representative Developers

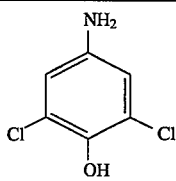
Developer D

The blocked chromogenic leuco dyes of the present invention can be prepared as follows: First, a coupler and a developer may be oxidatively reacted to form a chromogenic dye. Reduction of this dye, as for example, using hydrogen and a palladium on carbon catalyst forms the "chromogenic leuco dye", also often referred to as the "hydrogen leuco dye". Reaction of this chromogenic leuco dye with a "blocking reagent" forms the blocked chromogenic leuco dye. Scheme I exemplifies this route to form Blocked Leuco Dye B, using Coupler B as the coupler, 2-methyl-N,N-diethyl-p-phenylenediamine (Developer B) as the developer, and p-toluenesulfonylisocyanate as the "blocking reagent."

Scheme 1

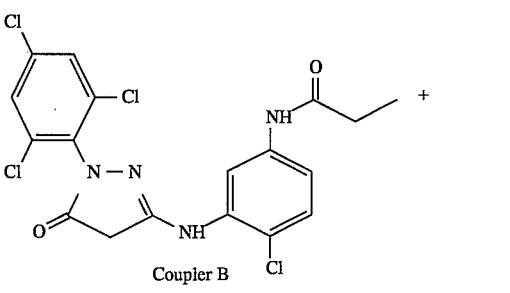
Coupler B

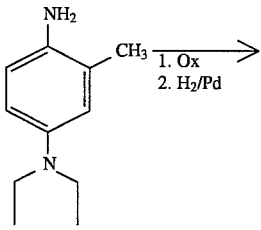
Developer B

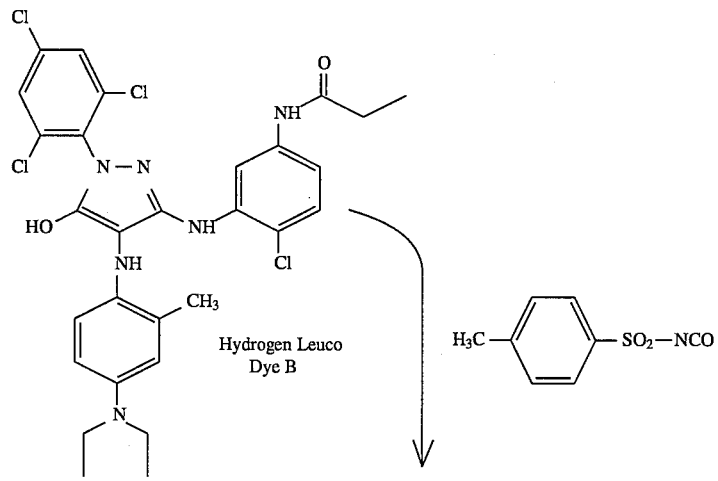
Hydrogen Leuco Dye B

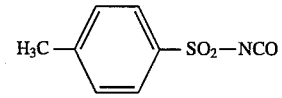

-continued
Scheme 1

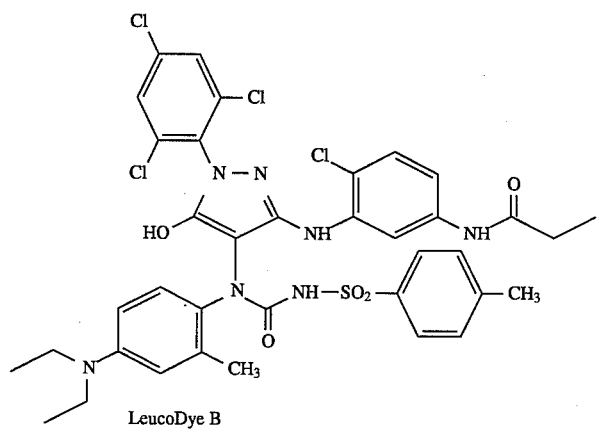

LeucoDye B

Representative blocked chromogenic leuco dyes of the present invention are shown below in Table III. These representations are exemplary and are not intended to be limiting. These exemplified compounds may be readily synthesized as shown later herein.

TABLE III
Representative Blocked Chromogenic Leuco Dyes

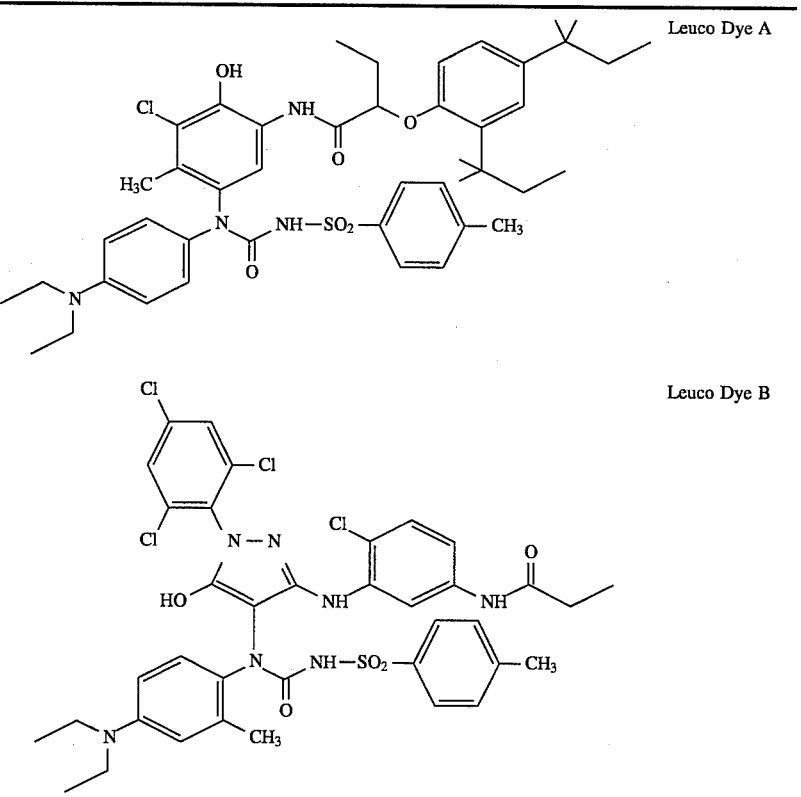

Leuco Dye A

Leuco Dye B

TABLE III-continued

Representative Blocked Chromogenic Leuco Dyes

Leuco Dye C

Leuco Dye D

Leuco Dye E

Leuco Dye F

The dyes formed from the blocked leuco dyes of the present invention in the various color-forming layers should, of course, be different. A difference of at least about 60 nm in reflective maximum absorbance is preferred. More preferably, the absorbance maximum of dyes formed will differ by at least about 80–100 nm. When three dyes are to be formed, two should preferably differ by at least these minimums, and the third should preferably differ from at least one of the other dyes by at least about 150 nm, and more preferably, by at least about 200 nm. Any leuco dye that can be blocked by the blocking groups of the present invention and that are capable of being oxidized by silver ion to form visible dyes are useful in the present invention as previously noted.

The total amount of blocked leuco dye used as a reducing agent utilized in the present invention should preferably be about 0.5–25 weight percent, and more preferably, about 1–10 weight percent, based upon the total weight of each individual layer in which the reducing agent is employed.

The Photosensitive Silver Halide

As noted above, the present invention includes a photosensitive silver halide in the photothermographic construction. The photosensitive silver halide can be any photosensitive silver halide, such as silver bromide, silver iodide, silver chloride, silver bromoiodide, silver chloro-bromoiodide, silver chlorobromide, etc. The photosensitive silver halide can be added to the emulsion layer in any fashion so long as it is placed in catalytic proximity to the organic silver compound which serves as a source of reducible silver.

The silver halide used in the present invention may be employed without modification. However, it can be chemically and spectrally sensitized in a manner similar to that used to sensitize conventional wet process silver halide or state-of-the-art heat-developable photographic materials. For example, it may be chemically sensitized with a chemical sensitizing agent, such as a compound containing sulfur, selenium, tellurium, etc., or a compound containing gold, platinum, palladium, ruthenium, rhodium, iridium, etc., a reducing agent such as a tin halide, etc., or a combination thereof. The details of these procedures are described in T. H. James, *The Theory of the Photographic Process*, Fourth Edition, Chapter 5, pp. 149–169. Suitable chemical sensitization procedures are also described in U.S. Pat. Nos. 1,623,499; 2,399,083; 3,297,447; and 3,297,446.

The photosensitive silver halides may be spectrally sensitized with various known dyes that spectrally sensitize silver halide. Non-limiting examples of sensitizing dyes that can be employed include cyanine dyes, merocyanine dyes, complex cyanine dyes, complex merocyanine dyes, holopolar cyanine dyes, hemicyanine dyes, styryl dyes, and hemioxanol dyes. Of these dyes, cyanine dyes, merocyanine dyes, and complex merocyanine dyes are particularly useful.

The light sensitive silver halide used in the present invention can be employed in a range of about 0.005 mole to about 0.5 mole and, preferably, from about 0.01 mole to about 0.15 mole per mole of non-photosensitive reducible silver salt. An appropriate amount of sensitizing dye added is generally about $10^{-10}$ to $10^{-1}$ mole, and preferably about $10^{-8}$ to $10^{-3}$ moles per mole of silver halide.

The Non-Photosensitive Reducible Silver Source Material

The non-photosensitive reducible silver source that can be used in the present invention can be any material that contains a source of reducible silver ions. Preferably, it is a silver salt which is comparatively stable to light and forms a silver image when heated to 80° C. or higher in the presence of an exposed photocatalyst (such as silver halide) and a reducing agent. Salts of organic acids, such as the silver salt of behenic acid, or other salts of organic materials, such as silver imidazolates, have been proposed. U.S. Pat. No. 4,260,677 discloses the use of complexes of inorganic or organic silver salts as non-photosensitive, reducible silver sources. Complexes of organic or inorganic silver salts, wherein the ligand has a gross stability constant for silver ion of about 4.0–10.0, are also useful in this invention.

Silver salts of organic acids, particularly silver salts of long chain fatty carboxylic acids, are preferred. The chains typically contain 10 to 30, preferably 15 to 28, carbon atoms. Suitable organic silver salts include silver salts of organic compounds having a carboxyl group. Examples thereof include a silver salt of an aliphatic carboxylic acid and a silver salt of an aromatic carboxylic acid. Preferred examples of the silver salts of aliphatic carboxylic acids include silver behenate, silver stearate, silver oleate, silver laurate, silver caproate, silver myristate, silver palmitate, silver maleate, silver fumarate, silver tartarate, silver furoate, silver linoleate, silver butyrate, silver camphorate, and mixtures thereof, etc. Silver salts that can be substituted with a halogen atom or a hydroxyl group also can be effectively used. Preferred examples of the silver salts of aromatic carboxylic acid and other carboxyl group-containing compounds include: silver benzoate, a silver-substituted benzoate, such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenylbenzoate, etc.; silver gallate; silver tannate; silver phthalate; silver terephthalate; silver salicylate; silver phenylacetate; silver pyromellitate; a silver salt of 3-carboxymethyl-4-methyl-4-thiazoline-2-thione or the like as described in U.S. Pat. No. 3,785,830; and a silver salt of an aliphatic carboxylic acid containing a thioether group as described in U.S. Pat. No. 3,330,663.

Silver salts of compounds containing mercapto or thione groups and derivatives thereof can also be used. Preferred examples of these compounds include: a silver salt of 3-mercapto-4-phenyl-1,2,4-triazole; a silver salt of 2-mercaptobenzimidazole; a silver salt of 2-mercapto-5-aminothiadiazole; a silver salt of 2-(2-ethylglycolamido)benzothiazole; a silver salt of thioglycolic acid, such as a silver salt of a S-alkylthioglycolic acid (wherein the alkyl group has from 12 to 22 carbon atoms); a silver salt of a dithiocarboxylic acid such as a silver salt of dithioacetic acid; a silver salt of thioamide; a silver salt of 5-carboxylic-1-methyl-2-phenyl-4-thiopyridine; a silver salt of mercaptotriazine; a silver salt of 2-mercaptobenzoxazole; a silver salt as described in U.S. Pat. No. 4,123,274, for example, a silver salt of a 1,2,4-mercaptothiazole derivative, such as a silver salt of 3-amino-5-benzylthio-1,2,4-thiazole; and a silver salt of a thione compound, such as a silver salt of 3-(2-carboxyethyl)-4-methyl-4-thiazoline-2-thione. Silver salts of acetylenes can also be used. Silver acetylides are described in U.S. Pat. Nos. 4,761,361 and 4,775,613.

Furthermore, a silver salt of a compound containing an imino group can be used. Preferred examples of these compounds include: silver salts of benzotriazole and substituted derivatives thereof, for example, silver methylbenzotriazole and silver 5-chlorobenzotriazole, etc.; silver salts of 1,2,4-triazoles or 1-H-tetrazoles as described in U.S. Pat. No. 4,220,709; and silver salts of imidazoles and imidazole derivatives.

It is also convenient to use silver half soaps. A preferred example of a silver half soap is an equimolar blend of silver behenate and behenic acid, which analyzes for about 14.5% silver and which is prepared by precipitation from an aqueous solution of the sodium salt of commercial behenic acid.

Transparent sheet materials made on transparent film backing require a transparent coating. For this purpose a silver behenate full soap, containing not more than about 4 or 5 percent of free behenic acid and analyzing for about 25.2 percent silver, can be used. The method used for making silver soap dispersions is well known in the art and is disclosed in *Research Disclosure*, April 1983, item 22812; *Research Disclosure*, October 1983, item 23419; and U.S. Pat. No. 3,985,565.

The silver halide may be "pre-formed" and mixed with the organic silver salt in a binder prior to use to prepare a coating solution. The silver halide may be pre-formed by any means, e.g., in accordance with U.S. Pat. No. 3,839,049. For example, it is effective to blend the silver halide and organic silver salt using a homogenizer for a long period of time. Materials of this type are often referred to as "pre-formed emulsions." Methods of preparing these silver halide and organic silver salts and manners of blending them are described in *Research Disclosure*, June 1978, item 17029; U.S. Pat. Nos. 3,700,458 and 4,076,539; and Japanese patent application Nos. 13224/74, 42529/76, and 17216/75.

Pre-formed silver halide emulsions when used in the material of this invention can be unwashed or washed to remove soluble salts. In the latter case the soluble salts can be removed by chill-setting and leaching or the emulsion can be coagulation washed, e.g., by the procedures described in U.S. Pat. Nos. 2,618,556; 2,614,928; 2,565,418; 3,241,969; and 2,489,341. The silver halide grains may have any crystalline habit including, but not limited to, cubic, tetrahedral, orthorhombic, tabular, laminar, platelet, etc. The silver halide grains may have a uniform ratio of halide throughout; they may have a graded halide content, with a continuously varying ratio of, for example, silver bromide and silver iodide; or they may be of the core-shell-type, having a discrete core of one halide ratio, and a discrete shell of another halide ratio.

It is also effective to use an in situ process, i.e., a process in which a halogen-containing compound is added to an organic silver salt to partially convert the silver of the organic silver salt to silver halide.

The silver halide and the non-photosensitive reducible silver source material that form a starting point of development should be in catalytic proximity, i.e., reactive association. By "catalytic proximity" or "reactive association" is meant that they should be in the same layer, in adjacent layers, or in layers separated from each other by an intermediate layer having a thickness of less than 1 micrometer (1 µm). It is preferred that the silver halide and the non-photosensitive reducible silver source material be present in the same layer.

Photothermographic emulsions containing pre-formed silver halide in accordance with this invention can be sensitized with chemical sensitizers, or with spectral sensitizers as described above.

The source of reducible silver material generally constitutes about 15 to about 70 percent by weight of the emulsion layer. It is preferably present at a level of about 30 to about 55 percent by weight of the emulsion layer.

The Binder

The photosensitive silver halide, the non-photosensitive reducible source of silver, the blocked leuco dye, and other addenda used in the present invention are generally added to at least one binder. The binder(s) that can be used in the present invention can be employed individually or in combination with one another. It is preferred that the binder be selected from polymeric materials, such as, for example, natural and synthetic resins that are sufficiently polar to hold the other ingredients of the emulsion in solution or suspension. The binder can be hydrophilic or hydrophobic, preferably it is hydrophobic.

A typical hydrophilic binder is a transparent or translucent hydrophilic colloid. Examples of hydrophilic binders include: a natural substance, for example, a protein such as gelatin, a gelatin derivative, a cellulose derivative, etc.; a polysaccharide such as starch, gum arabic, pullulan, dextrin, etc.; and a synthetic polymer, for example, a water-soluble polyvinyl compound such as polyvinyl alcohol, polyvinyl pyrrolidone, acrylamide polymer, etc. Another example of a hydrophilic binder is a dispersed vinyl compound in latex compound which is used for the purpose of increasing dimensional stability of a photographic element.

Examples of typical hydrophobic binders are polyvinyl acetals, polyvinyl chloride, polyvinyl acetate, cellulose acetate, polyolefins, polyesters, polystyrene, polyacrylonitrile, polycarbonates, methacrylate copolymers, maleic anhydride ester copolymers, butadiene-styrene copolymers, and the like. Copolymers, e.g. terpolymers, are also included in the definition of polymers. The polyvinyl acetals, such as polyvinyl butyral and polyvinyl formal, and vinyl copolymers such as polyvinyl acetate and polyvinyl chloride are particularly preferred.

The binders are preferably used at a level of about 20–80 percent by weight of the emulsion layer, and more preferably at a level of about 30–55 percent by weight. Where the proportions and activities of the blocked leuco dyes of the present invention require a particular developing time and temperature, the binder should be able to withstand those conditions. Generally, it is preferred that the binder not decompose or lose its structural integrity at 200° F. (90° C.) for 30 seconds, and more preferred that it not decompose or lose its structural integrity at 300° F. (149° C.) for 30 seconds.

Optionally, these polymers may be used in combination of two or more thereof. Such a polymer is used in an amount sufficient to carry the components dispersed therein, that is, within the effective range of the action as the binder. The effective range can be appropriately determined by one skilled in the art.

Photothermographic Formulations

The formulation for the photothermographic emulsion layer can be prepared by dissolving and dispersing the binder, the photosensitive silver halide, the non-photosensitive reducible source of silver, the blocked leuco dye reducing agent for the non-photosensitive reducible silver source, and optional additives, in an inert organic solvent, such as, for example, toluene, 2-butanone, or tetrahydrofuran.

The use of "toners" or derivatives thereof which improve the image, is highly desirable, but is not essential to the element. Toners can be present in an amount of about 0.01–10 percent by weight of the emulsion layer, preferably about 0.1–10 percent by weight. Toners are well known materials in the photothermographic art, as shown in U.S. Pat. Nos. 3,080,254; 3,847,612; and 4,123,282.

Examples of toners include: phthalimide and N-hydroxyphthalimide; cyclic imides such as succinimide, pyrazoline-5-ones, quinazolinone, 1-phenylurazole, 3-phenyl-2-pyrazoline-5-one, and 2,4-thiazolidinedione; naphthalimides such as N-hydroxy-1,8-naphthalimide; cobalt complexes such as cobaltic hexamine trifluoroacetate; mercaptans such as 3-mercapto-1,2-triazole, 2,4-dimercaptopyrimidine, 3-mercapto-4,5-diphenyl-1,2,4-triazole and 2,5-dimercapto-1,3,4-thiadiazole; N-(aminomethyl)aryldicarboximides such as (N,N-dimethylaminomethyl)phthalimide, and N-(dimethylaminomethyl)naphthalene-2,3-dicarboximide; a combination of blocked pyrazoles, isothiuronium derivatives, and certain photobleach agents such as a combination of N,N'-hexamethylene-bis(1-carbamoyl-3,5-dimethylpyrazole), 1,8-(3,6-diaza-octane)bis(isothiuronium)trifluoroacetate, and 2-(tribromomethylsulfonyl benzothiazole); merocyanine dyes such as 3-ethyl-5-[(3-ethyl-2-benzothiazolinylidene)-1-methyl-ethylidene]-2-thio-2,4-o-azolidinedione; phthalazinone, phthalazinone derivatives, or metal salts or these derivatives, such as 4-(1-naphthyl)phthalazinone, 6-chlorophthalazinone, 5,7-dimethoxyphthalazinone, and 2,3-dihydro-1,4-phthalazinedione; a combination of phthalazine plus one or more phthalic acid derivatives such as phthalic acid, 4-methylphthalic acid, 4-nitrophthalic acid, and tetrachlorophthalic anhydride, quinazolinediones, benzoxazine or naphthoxazine derivatives; rhodium complexes functioning not only as tone modifiers but also as sources of halide ion for silver halide formation in situ, such as ammonium hexachlororhodate (III), rhodium bromide, rhodium nitrate, and potassium hexachlororhodate (III); inorganic peroxide and persulfates such as ammonium peroxydisulfate and hydrogen peroxide; benzoxazine-2,4-diones such as 1,3-benzoxazine-2,4-dione, 8-methyl-1,3-benzoxazine-2,4-dione, and 6-nitro-1,3-benzoxazine-2,4-dione; pyrimidines and asym-triazines such as 2,4-dihydroxypyrimidine, 2-hydroxy-4-aminopyrimidine, and azauracil; and tetrazapentalene derivatives such as 3,6-dimercapto-1,4-diphenyl-1H,4H-2,3a5,6a-tetrazapentalene and 1,4-di-(o-chlorophenyl)-3,6-dimercapto-1H,4H-2,3a,5,6a-tetrazapentalene.

The photothermographic elements used in this invention can be further protected against the additional production of fog and can be stabilized against loss of sensitivity during storage. While not necessary for the practice of the invention, it may be advantageous to add mercury (II) salts to the emulsion layer(s) as an antifoggant. Preferred mercury (II) salts for this purpose are mercuric acetate and mercuric bromide.

Other suitable antifoggants and stabilizers, which can be used alone or in combination, include the thiazolium salts described in U.S. Pat. Nos. 2,131,038 and 2,694,716; the azaindenes described in U.S. Pat. No. 2,886,437; the triazaindolizines described in U.S. Pat. No. 2,444,605; the mercury salts described in U.S. Pat. No. 2,728,663; the urazoles described in U.S. Pat. No. 3,287,135; the oximes described in British Patent No. 623,448; the polyvalent metal salts described in U.S. Pat. No. 2,839,405; the isothiourea compounds described in U.S. Pat. No. 3,220,839; and palladium, platinum and gold salts described in U.S. Pat. Nos. 2,566,263 and 2,597,915.

Photothermographic elements of the invention can contain plasticizers and lubricants such as polyalcohols and diols of the type described in U.S. Pat. No. 2,960,404; fatty acids or esters such as those described in U.S. Pat. Nos. 2,588,765 and 3,121,060; and silicone resins such as those described in British Patent No. 955,061.

The photothermographic elements of the present invention can also include image dye stabilizers. Such image dye stabilizers are illustrated by U.K. Patent No. 1,326,889; and U.S. Pat. Nos. 3,432,300; 3,574,627; 3,573,050; 3,764,337; and 4,042,394.

Photothermographic elements according to the present invention can be used in photographic elements that contain light-absorbing materials, acutance, antihalation, and filter dyes such as those described in U.S. Pat. Nos. 3,253,921; 2,274,782; 2,527,583; 2,956,879; and 5,266,452. If desired, the dyes can be mordanted, for example, as described in U.S. Pat. No. 3,282,699. They can also contain matting agents such as starch, titanium dioxide, zinc oxide, silica, and polymeric beads including beads of the type described in U.S. Pat. Nos. 2,992,101 and 2,701,245. Furthermore, they can contain antistatic or conducting layers, such as layers that comprise soluble salts, e.g., chlorides, nitrates, etc., evaporated metal layers, ionic polymers such as those described in U.S. Pat. No. 3,206,312, or insoluble inorganic salts such as those described in U.S. Pat. No. 3,428,451.

Photothermographic Constructions

The photothermographic elements of this invention can be constructed of one or more layers on a substrate. Single layer constructions should contain the silver halide, the non-photosensitive, reducible silver source material, the blocked leuco dye, and binder as well as optional materials such as toners, coating aids, and other adjuvants. Two-layer constructions should contain silver halide and non-photosensitive, reducible silver source in one emulsion layer (usually the layer adjacent to the substrate) and some of the other ingredients in the second layer or both layers, although two layer constructions comprising a single emulsion layer coating containing all the ingredients and a protective topcoat are envisioned. Multicolor photothermographic dry silver constructions can contain sets of these bilayers for each color or they can contain all ingredients within a single layer, as described in U.S. Pat. No. 4,708,928. In the case of multilayer, multicolor photothermographic elements, the various emulsion layers are generally maintained distinct from each other by the use of functional or non-functional barrier layers between the various photosensitive layers, as described in U.S. Pat. No. 4,460,681.

Development conditions will vary, depending on the construction used, but will typically involve heating the imagewise exposed material at a suitably elevated temperature. When used in a photothermographic element, the latent image obtained after exposure of the heat-sensitive construction can be developed by heating the material at a moderately elevated temperature of, for example, about 80°–250° C., preferably about 120°–200° C., for a sufficient period of time, generally about 1 second to about 2 minutes. Heating may be carried out by the typical heating means such as a hot plate, an iron, a hot roller, a heat generator using carbon or titanium white, or the like.

In some methods, the development is carried out in two steps. Thermal development takes place at a higher temperature, e.g., about 150° C. for about 10 seconds, followed by thermal diffusion at a lower temperature, e.g., about 80° C., in the presence of a transfer solvent. The second heating step at the lower temperature prevents further development and allows the dyes that are already formed to diffuse out of the emulsion layer to the receptor layer.

Photothermographic emulsions used in this invention can be coated by various coating procedures including wire wound rod coating, dip coating, air knife coating, curtain coating, or extrusion coating using hoppers of the type described in U.S. Pat. No. 2,681,294. If desired, two or more layers can be coated simultaneously by the procedures described in U.S. Pat. No. 2,761,791 and British Patent No. 837,095. Typical wet thickness of the emulsion layer can be about 10–100 micrometers (μm), and the layer can be dried in forced air at a temperature of about 20°–100° C. It is preferred that the thickness of the layer be selected to provide maximum image densities greater than about 0.2, and, more preferably, in the range of about 0.5 to 2.5, as measured by a MacBeth Color Densitometer Model TD 504 using the color filter complementary to the dye color.

Additionally, it may be desirable in some instances to coat different emulsion layers on both sides of a transparent substrate, especially when it is desirable to isolate the imaging chemistries of the different emulsion layers.

Barrier layers, preferably comprising a polymeric material, can also be present in the photothermographic element of the present invention. Polymers for the material of the barrier layer can be selected from natural and synthetic polymers such as gelatin, polyvinyl alcohols, polyacrylic acids, sulfonated polystyrene, and the like. The polymers can optionally be blended with barrier aids such as silica. Alternatively, the formulation can be spray-dried or encapsulated to produce solid particles, which can then be redispersed in a second, possibly different, binder and then coated onto the support. The formulation for the emulsion layer can also include coating aids such as fluoroaliphatic polyesters.

Photothermographic emulsions used in the invention can be coated on a wide variety of supports. The support or substrate can be selected from a wide range of materials depending on the imaging requirement. Substrates may be transparent or opaque. Typical supports include polyester film, subbed polyester film, poly(ethylene terephthalate) film, cellulose nitrate film, cellulose ester film, polyvinyl acetal film, polycarbonate film and related or resinous materials, as well as glass, paper, metal, and the like. Typically, a flexible support is employed, especially a paper support, which can be partially acetylated or coated with baryta and/or an α-olefin polymer, particularly a polymer of an α-olefin containing 2 to 10 carbon atoms such as polyethylene, polypropylene, ethylene-butene copolymers, and the like. Preferred polymeric materials for the support include polymers having good heat stability, such as polyesters. A particularly preferred polyester is poly(ethylene terephthalate). A substrate with a backside resistive heating layer can also be used in color photothermographic imaging systems such as shown in U.S. Pat. Nos. 4,460,681 and 4,374,921.

The Image-Receiving Layer

When the reactants and reaction products of photothermographic systems that contain compounds capable of being oxidized to form a dye remain in contact after imaging, several problems can result. For example, thermal development often forms turbid and hazy color images because of dye contamination by the reduced metallic silver image on the exposed area of the emulsion. In addition, the resulting prints tend to develop color in unimaged background areas. This "background stain" is caused by slow reaction between the dye-forming compound and reducing agent during storage. It is therefore desirable to transfer the dye formed upon imaging to a receptor, or image-receiving layer.

Thus, the photothermographic element can further include an image-receiving layer. Images derived from the photothermographic elements employing leuco dyes capable of being oxidized to form a dye are typically transferred to an image-receiving layer.

If used, dyes generated during thermal development of light-exposed regions of the emulsion layers migrate under development conditions into the an image-receiving, i.e., dye-receiving, layer wherein they are retained. The dye-receiving layer can be composed of a polymeric material having affinity for the dyes employed. Necessarily, it will vary depending on the ionic or neutral characteristics of the dyes.

The image-receiving layer of this invention can be any flexible or rigid, transparent layer made of thermoplastic polymer. The image-receiving layer preferably has a thickness of at least about 0.1 μm, more preferably about 1–10 μm, and a glass transition temperature ($T_g$) of about 20°–200° C. In the present invention, any thermoplastic polymer or combination of polymers can be used, provided the polymer is capable of absorbing and fixing the dye. The polymer may include dye mordants to fix the dye. Alternatively, the polymer itself may act as a dye mordant in which no additional fixing agents are required. Thermoplastic polymers that can be used to prepare the image-receiving layer include polyesters, such as polyethylene terephthalates; polyolefins, such as polyethylene; cellulosics, such as cellulose acetate, cellulose butyrate, and cellulose propionate; polystyrene; polyvinyl chloride; polyvinylidine chloride; polyvinyl acetate; copolymer of vinyl chloride-vinyl acetate; copolymer of vinylidene chloride-acrylonitrile; copolymer of styrene-acrylonitrile; and the like.

The image-receiving layer can be prepared by dissolving at least one thermoplastic polymer in an organic solvent (e.g., 2-butanone, acetone, tetrahydrofuran) and applying the resulting solution to a support base or substrate by various coating methods known in the art, such as curtain coating, extrusion coating, dip coating, air-knife coating, hopper coating, and any other coating method used for coating solutions. After the solution is coated, the image-receiving layer is dried (e.g., in an oven) to drive off the solvent. The image-receiving layer can be a permanent part of the construction or it can be removable. When an integral part of the photothermographic element, it is usually separated from the photothermographic emulsion layers by an opacifying layer. Alternatively, the image-receiving layer can be strippably adhered to the photothermographic element and subsequently peeled from the construction. Strippable image-receiving layers are described in U.S. Pat. No. 4,594,307.

Selection of the binder and solvent to be used in preparing the emulsion layer significantly affects the strippability of the image-receiving layer from the photosensitive element. Preferably, the binder for the image-receiving layer is impermeable to the solvent used for coating the emulsion layer and is incompatible with the binder used for the emulsion layer. The selection of the preferred binders and solvents results in weak adhesion between the emulsion layer and the image-receiving layer and promotes good strippability of the emulsion layer.

The photothermographic element can also include coating additives to improve the strippability of the emulsion layer. For example, fluoroaliphatic polyesters dissolved in ethyl acetate can be added in an amount of about 0.02–0.5 weight percent of the emulsion layer, preferably about 0.1–0.3 weight percent. A representative example of such a fluoroaliphatic polyester is "Fluorad™ FC 431" (a fluorinated surfactant available from Minnesota Mining and Manufacturing Company, St. Paul, Minn.). Alternatively, a coating additive can be added to the image-receiving layer in the same weight range to enhance strippability. No solvents need to be used in the stripping process. The strippable layer preferably has a delaminating resistance of about 1–50 g/cm and a tensile strength at break greater than, preferably at least two times greater than, its delaminating resistance.

Preferably, the image-receiving layer is adjacent to the emulsion layer in order to facilitate transfer of the dye that forms after the imagewise exposed emulsion layer is subjected to thermal development, for example, in a heated shoe-and-roller-type or heated drum-type heat processor.

Photothermographic multi-layer constructions containing blue-sensitive emulsions containing a yellow leuco dye can be overcoated with green-sensitive emulsions containing a magenta leuco dye. These layers can in turn be overcoated with a red-sensitive emulsion layer containing a cyan leuco dye. Imaging and heating form the yellow, magenta, and cyan images in an imagewise fashion. Color-forming layers can be maintained distinct from each other by the use of functional or non-functional barrier layers between the various photosensitive layers as described in U.S. Pat. No. 4,460,681. False color address, such as that shown in U.S. Pat. No. 4,619,892, can also be used rather than blue-yellow, green-magenta, or red-cyan relationships between sensitivity and dye formation. False color address is particularly useful when imaging is performed using longer wavelengths light sources, especially red or near infra-red, to enable digital address by lasers and laser diodes. The dyes so formed may migrate to an image-receiving layer.

If desired, the colored dyes formed in the emulsion layer can be transferred onto a separately coated image-receiving sheet by placing the exposed emulsion layer in intimate face-to-face contact with the image-receiving sheet and heating the resulting composite construction. Good results can be achieved in this second embodiment when the layers are in uniform contact for a period of time of about 0.5–300 seconds at a temperature, of about 80°–250° C.

In another embodiment, a multi-colored image can be prepared by superimposing in register a single image-receiving sheet successively with two or more imagewise exposed photothermographic elements, each of which forms a dye of a different color, and heating to transfer the thus formed dyes as described above. This method is particularly suitable for the production of color proofs especially when the dyes formed have hues that match the internationally agreed standards for color reproduction. These are known as Standard Web Offset Press or SWOP colors. Dyes with this property are disclosed in U.S. Pat. No. 5,023,229. In this embodiment, the photothermographic elements are preferably all sensitized to the same wavelength range regardless of the color of the dye formed. For example, the elements can be sensitized to ultraviolet radiation with a view toward contact exposure on conventional printing frames, or they can be sensitized to longer wavelengths, especially red or near infra-red, to enable digital address by lasers and laser diodes. As noted above, false color address is again particularly useful when imaging is performed using longer wavelength light sources, especially red or near infrared light sources, to enable digital address by lasers and laser diodes.

The complete disclosures of all patents, patent documents, and publications listed herein are incorporated by reference. Reasonable modifications and variations are possible from the foregoing disclosure without departing from either the spirit or scope of the present invention as defined by the claims. Objects and advantages of this invention will now be illustrated by the following examples, but the particular materials and amounts thereof recited in these examples, as well as other conditions and details, should not be construed to unduly limit this invention.

EXAMPLES

All materials used in the following examples were readily available from standard commercial sources, such as Aldrich Chemical Co. (Milwaukee, Wis.) unless otherwise specified. All percentages are by weight unless otherwise indicated.

EXAMPLES 1

Preparation of Blocked Cyan Chromogenic Leuco Dye A

Cyan Coupler K (5.00 g, 10.11 mmol) was dissolved in 250 mL of chloroform. A solution of Developer C (4.223 g, 19.67 mmol) and 1.398 g (28.25 mmol) of sodium carbonate in 40 mL of water was added with vigorous agitation. A solution of potassium ferricyanide (14.981 g, 45.50 mmol) and 5.487 g (81.90 mmol) of sodium carbonate in 150 mL of water was added dropwise to the reaction solution. After 30 minutes, the solution was transferred to a separatory funnel and the organic layer was removed and washed three times with water. The solution was filtered, dried over anhydrous magnesium sulfate, filtered, and the chloroform was removed in vacuo to afford the desired cyan chromogenic leuco dye. The material was used in the next step without further purification.

To 2.0 g (3.2 mmol) of this cyan chromogenic leuco dye in 100 mL of dry tetrahydrofuran was added 5% palladium on carbon. The mixture was hydrogenated for 45 minutes at room temperature and 2 atmospheres pressure. A colorless solution resulted. To this was added the blocking reagent p-toluenesulfonyl isocyanate (0.699 g, 3.55 mmol). This mixture was stirred overnight at room temperature and then filtered to remove the palladium catalyst. The solvent was removed in vacuo. The residue was purified by flash chromatography on silica gel with a petroleum ether/ethyl acetate solvent system beginning with 5% ethyl acetate to remove the first fraction which was the starting cyan dye and gradually increasing the polarity to remove the desired cyan blocked leuco dye. The desired blocked leuco dye A (0.40 g) was obtained. TLC indicated the sample contained a small amount of the corresponding cyan dye.

EXAMPLE 2

Preparation of Blocked Magenta Chromogenic Leuco Dye B

Magenta Coupler B (5.00 g, 10.87 mmol) was dissolved in 250 mL of chloroform. A solution of the hydrochloride salt of Developer B (4.223 g, 19.67 mmol) and 2.994 g (28.25 mmol) of sodium carbonate in 40 mL of water was added with vigorous agitation. A solution of potassium ferricyanide (16.099 g, 48.90 mmol) and 5.897 g (88.01 mmol) of sodium carbonate in 150 mL of water was added dropwise to the reaction solution. After 30 minutes, the solution was transferred to a separatory funnel and the organic layer was removed and washed three times with water. The solution was filtered, dried over anhydrous magnesium sulfate, filtered, and the chloroform was removed in vacuo. $^1$H NMR indicated the desired magenta chromogenic leuco dye to be present along with impurities. Attempted recrystallization from ethyl acetate/hexane was unsuccessful. The material was used in the next step without further purification.

To 2.0 g (3.2 mmol) of this magenta chromogenic leuco dye in 100 mL of dry tetrahydrofuran was added 5% palladium on carbon. The mixture was hydrogenated at room temperature and 2 atmospheres pressure until a colorless solution was obtained. The flask was purged with nitrogen and the blocking reagent p-toluenesulfonyl isocyanate (0.684 g, 3.47 mmol) was added. This mixture was stirred overnight at room temperature and then filtered to remove the palladium catalyst. The solvent was removed in vacuo. The residue was purified by flash chromatography on silica gel with a 10% ethyl acetate/petroleum ether solvent system to remove the unblocked magenta dye. To remove the blocked leuco dye B, the polarity of the solvent system was gradually increased until the solvent system was 100% ethyl acetate. The desired magenta blocked leuco dye B was obtained with a small amount of the corresponding magenta dye as evidenced by TLC.

EXAMPLE 3

Preparation of Blocked Yellow Chromogenic Leuco Dye C

To 2.0 g (3.2 mmol) of a yellow chromogenic leuco dye, prepared by the coupling of Yellow Coupler H and Developer C in a manner similar to that described in Examples 1 and 2, in 100 mL of dry tetrahydrofuran was added 5% palladium on carbon. The mixture was hydrogenated at room temperature and 2 atmospheres pressure until a colorless solution resulted. To this was added the blocking reagent p-toluenesulfonyl isocyanate (0.699 g, 3.55 mmol). This mixture was stirred overnight at room temperature and then was filtered to remove the palladium catalyst. The solvent was removed in vacuo. TLC showed the presence of a yellow leuco dye.

EXAMPLE 4

Preparation of Blocked Yellow Chromogenic Leuco Dye D

To 1.0 g (2.3 mmol) of a yellow chromogenic leuco dye, prepared by the coupling of Yellow Coupler F and Developer C in a manner similar to that described in Examples 1 and 2, in 25 mL of dry tetrahydrofuran was added zinc dust (2.0 g, 30 mmol) and chlorotrimethylsilane (0.63 mL, 5.0 mmol). The mixture was heated at refluxing temperature for 10 minutes. To this was added the blocking reagent p-toluenesulfonyl isocyanate (0.55 g, 2.6 mmol). The mixture was refluxed for 1.5 hours and then allowed to cool to room temperature. Methanol (10 mL) was added and the mixture was stirred for 15 minutes. The reaction mixture was then filtered through a 1 cm pad of Florisil® (available from Aldrich Chemical Co.) followed by 100 mL of ethyl acetate. The combined filtrates were washed twice with a saturated solution of sodium bicarbonate in water (25 mL), dried over magnesium sulfate and filtered. The solvent was removed in vacuo leaving the blocked leuco dye D as a light tan colored solid. Mass spectroscopy and NMR were in agreement with the assigned structure.

EXAMPLE 5

Preparation of Blocked Yellow Chromogenic Leuco Dye E

To 1.0 g (2.3 mmol) of a yellow chromogenic leuco dye, prepared by the coupling of Coupler F and Developer C in a manner similar to that described in Examples 1 and 2, in 25 mL of dry tetrahydrofuran was added zinc dust (2.0 g, 30 mmol) and chlorotrimethylsilane (0.63 mL, 5.0 mmol). The mixture was heated at refluxing temperature for 10 minutes. To this was added the blocking reagent p-methoxybenzenesulfonyl isocyanate (0.55 g, 2.6 mmol, prepared as described by H. Ulrich et al., Angew. Chem., Int. Ed., 5, 704 (1966)). The mixture was refluxed for 1.5 hours and then allowed to cool to room temperature. Methanol (10 mL) was added and the mixture was stirred for 15 minutes. The reaction mixture was then filtered through a 1 cm pad of Florisil® followed by 100 mL of ethyl acetate. The combined filtrates were washed twice with a saturated solution of sodium bicarbonate in water (25 mL), dried over magnesium sulfate and filtered. The solvent was removed in vacuo leaving the blocked leuco dye E as a light tan colored solid. NMR was in agreement with the assigned structure.

EXAMPLE 6

Preparation of Blocked Cyan Chromogenic Leuco Dye F

To 1.0 g (2.5 mmol) of a cyan chromogenic leuco dye, prepared by the coupling of Cyan Coupler M and Developer C in a manner similar to that described in Examples 1 and 2, in 25 mL of dry tetrahydrofuran was added zinc dust (2.0 g, 30 mmol) and chlorotrimethylsilane (0.63 mL, 5.0 mmol). The mixture was heated at refluxing temperature for 10 minutes. To this was added the blocking reagent p-toluenesulfonyl isocyanate (0.55 g, 2.6 mmol). The mixture was refluxed for 1.5 hours and then allowed to cool to room temperature. Methanol (10 mL) was added and the mixture was stirred for 15 minutes. The reaction mixture was then filtered through a 1 cm pad of Florisil® followed by 100 mL of ethyl acetate. The combined filtrates were washed twice with a saturated solution of sodium bicarbonate in water (25 mL), dried over magnesium sulfate and filtered. The solvent was removed in vacuo leaving the blocked leuco dye F as a light tan colored solid. NMR was in agreement with the assigned structure.

EXAMPLE 7

Test For The Presence of Leuco Dyes

All of the above leuco dyes gave the corresponding cyan, magenta, or yellow color when subjected to the following test conditions: the blocked leuco dyes were chromatographed on thin layer silica gel chromatography plates using ethyl acetate/petroleum ether or dichloromethane/ethyl acetate solvent systems. Following development, the plates were placed in a 5% aqueous sodium carbonate solution for approximately five seconds and then placed in a 3% aqueous potassium ferricyanide solution for approximately five seconds. The plates were rinsed under water. Following this treatment the initially colorless leuco dye spot on the silica gel plate was converted to a cyan, magenta, or yellow color.

EXAMPLE 8

Preparation of "Dry Silver" Photothermographic Formulations

A dispersion of a silver behenate full soap (prepared as described in U.S. Pat. No. 3,839,049) containing preformed silver halide grains (0.05 micron grain size, 9.0 mol-% silver halide, and 98%:2% Br:I ratio of halides) was homogenized to 11.94% solids in a mixture of ethanol and toluene (76:24) and 0.48% polyvinyl butyral (Butvar™ B-76 available from Monsanto, St. Louis, Mo.). To 200.0 g of the silver full soap dispersion was added 40.0 g of ethanol. After 10 minutes of mixing, an additional 32 g of the polyvinyl butyral was added. After 30 minutes, 1.65 mL of a methanol solution of pyridinium hydrobromide perbromide (0.3 g/3 mL) was added and mixed for 3 hours. A final addition of 1.3 mL of a 10% calcium bromide solution was mixed for 60 minutes. To 4.5 g of this silver solution was added 0.35 mL of the sensitizing dye shown below (0.81 g/40 mL of methanol and 10 mL toluene, prepared according to U.S. Pat. No. 4,123,282).

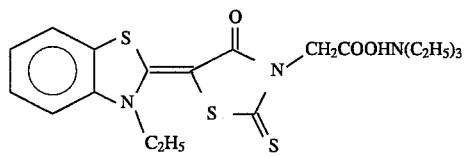

After 30 minutes, a solution of 2-(4-chlorobenzoyl)benzoic acid (0.02 g), N,N-bis[2-(4,6-tribromomethyl-1,3,5-triazino)]-1,3-dipiperidinopropane (0.025 g, prepared as described in Applicants' Assignee's copending allowed U.S. patent application Ser. No. 08/051,085, filed Apr. 21, 1993) and tetrahydrofuran (0.8 g) was added to the blue-sensitized silver premix. The structure of the dipiperidinopropane is as follows:

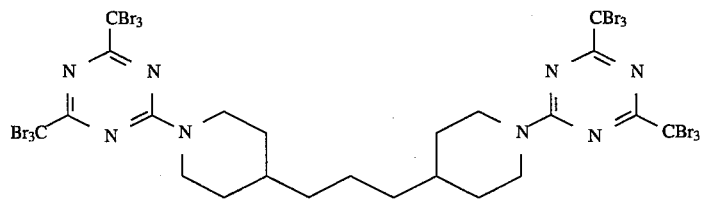

After 15 minutes, a blocked developer solution containing $1.126 \times 10^{-4}$ mol of a blocked leuco dye (dye D, E, or F), tetrahydrofuran (2.0 g), and fluoroaliphatic polyester surfactant Fluorad™ FC-431 (0.1 mL, available from Minnesota Mining and Manufacturing Company, St. Paul, Minn.) was added to the blue-sensitized silver premix. The resultant solution is referred to herein as the silver halide solution.

colored dye (yellow for dyes D and E or cyan for dye F) that was transferred by diffusion to a receptor layer.

| Toner | Exposure Condition | Processing Conditions | Donor + Receptor | | | Receptor | | |
|---|---|---|---|---|---|---|---|---|
| | | | Dmin[1] | Dmax[2] | Speed[3] | Dmin[1] | Dmax[2] | Speed[3] |
| Blocked Leuco Dye D | | | | | | | | |
| PHZ/4MPA/TBPAN | $1 \times 10^{-3}$ | 30sec/280° F. | 0.80 | 1.18 | 1.49 | 0.53 | 0.68 | — |
| PHZ/4MPA/TBPAN | $2 \times 10^{-3}$ | 30sec/280° F. | 0.78 | 1.21 | 1.09 | 0.50 | 0.73 | 2.04 |
| PHZ/4MPA/TBPAN | $1 \times 10^{-3}$ | 40sec/280° F. | 0.85 | 1.28 | 1.53 | 0.55 | 0.75 | 2.35 |
| Blocked Leuco Dye E | | | | | | | | |
| PHZ/4MPA/TBPAN | $1 \times 10^{-3}$ | 30sec/280° F. | 0.79 | 1.26 | 1.37 | 0.50 | 0.69 | — |
| PHZ/4MPA/TBPAN | $2 \times 10^{-3}$ | 30sec/280° F. | 0.77 | 1.25 | 1.15 | 0.50 | 0.67 | 2.04 |
| PHZ/4MPA/TBPAN | $1 \times 10^{-3}$ | 40sec/280° F. | 0.90 | 1.30 | 1.42 | 0.56 | 0.77 | 2.58 |
| Blocked Leuco Dye F[4] | | | | | | | | |
| PAZ | $2 \times 10^{-3}$ | 10sec/280° F. | 1.05 | 1.25 | 2.71 | 0.65 | 0.71 | — |
| PAZ | $1 \times 10^{-3}$ | 20sec/280° F. | 1.13 | 1.34 | 2.68 | 0.72 | 0.78 | — |
| PHZ/4MPA/TBPAN | $1 \times 10^{-3}$ | 10sec/280° F. | 1.15 | 1.40 | 1.70 | 0.65 | 0.75 | — |
| PHZ/4MPA/TBPAN | $2 \times 10^{-3}$ | 10sec/280° F. | 1.15 | 1.41 | 1.54 | 0.67 | 0.75 | — |
| PHZ/4MPA/TBPAN | $1 \times 10^{-3}$ | 20sec/280° F. | 1.22 | 1.43 | — | 0.73 | 0.82 | — |

[1]Dmin is the average of the 8 lowest density values on the exposed side of the material.
[2]Dmax is the highest density value on the exposed side of the material.
[3]Speed is the Log exposure (in ergs/cm$^2$) corresponding to a density of 0.20 above Dmin.
[4]Dmin is high because of contamination by the corresponding dye.

A receptor solution was prepared containing 15% by weight VYNS-3™ (copolymer of vinylchloride and vinylacetate available from Union Carbide, Danbury, Conn.) in methyl ethyl ketone and toluene (50:50). This solution was coated onto a filled polyester (sold under the tradename Melinex™ 994 by ICI, Wilmington, Del.) base at a wet thickness of 3 mils. The silver halide solution was coated at a wet thickness of 2 mils onto the receptor layer.

A topcoat solution was prepared containing 5.9% cellulose acetate, 1.33% Rohm and Haas Acryloid™ A-21 in an acetone, isopropyl alcohol, and methanol mixture (11.67:2.72:1 ). For contain examples, the following toners were added to 123.75 g of the topcoat solution: phthalazine (0.436 g, PHZ), 4-methylphthalic acid (0.235 g, 4-MPA), and tetrabromophthalic anhydride (0.372 g, TBPAN). If these toners were used then phthalazinone was eliminated from the silver halide solution. The topcoat solution was coated at a wet thickness of 3 mils over the silver halide layer.

All the layers were dried for 5 minutes at 180° F. (82° C.). The samples were exposed using an EG&G Sensitometer for $10^{-3}$ second with a xenon flash through a 47B Wratten filter and a 0–3 continuous wedge. The coatings were processed with heat at dwell times of 10–60 seconds and a dwell temperature of 280° F. (138° C.) using a 3M Model 9009 Dry Silver Processor that had been modified to permit variable dwell times.

The sensitometric responses for these compounds are shown below. Speed was measured as the log exposure corresponding to a density of 0.20 above Dmin. A photothermographic response was obtained by the reduction of silver and the oxidation of the blocked leuco dye to form a These results demonstrate the imaging capabilities of the leuco dyes of the present invention.

The disclosures of all publications, patents, and patent applications listed herein am incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A photothermographic element comprising a support bearing at least one heat-developable, photosensitive, image-forming photothermographic emulsion layer comprising:

(a) a photosensitive silver halide;

(b) a non-photosensitive, reducible source of silver;

(c) a leuco dye reducing agent; and (d) a binder;

wherein the leuco dye reducing agent comprises a chromogenic leuco dye compound of the general formula:

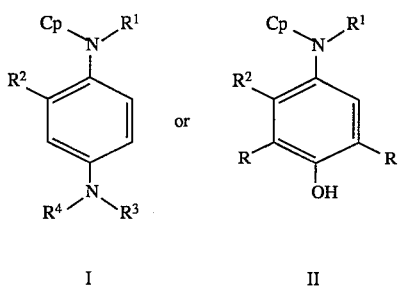

I    II wherein:
(a) R is hydrogen or halogen;
(b) $R^1$ is a C(O)—NH—SO$_2$—$R^5$ group, wherein $R^5$ is an aliphatic group containing 1–50 carbon atoms or an aromatic group containing 5–50 carbon atoms;
(c) $R^2$ is a hydrogen atom, an alkoxy group, or an alkyl group;
(d) $R^3$ and $R^4$ are each independently an aliphatic group, an aromatic group, or an -X-Y group, wherein X is an alkylene group containing 1–4 carbon atoms, and Y is a cyano group, a halogen atom, an alkoxy group containing 1–20 carbon atoms, or —OH; and
(e) Cp is a coupler group.

2. The photothermographic element of claim 1 wherein $R^5$ is an alkyl group containing 1–20 carbon atoms or an aryl group containing 5–30 carbon atoms.

3. The photothermographic element of claim 2 wherein $R^5$ is a phenyl group.

4. The photothermographic element of claim 3 wherein $R^5$ is p-tolyl.

5. The photothermographic element of claim 1 wherein $R^2$ is a hydrogen atom, an alkyl group containing 1–20 carbon atoms, or an alkoxy group containing 1–20 carbon atoms.

6. The photothermographic element of claim 1 wherein $R^3$ and $R^4$ are each independently an alkyl group containing 1–20 carbon atoms or an aromatic group containing 5–30 carbon atoms.

7. The photothermographic element of claim 1 wherein the coupler group is a photographic coupler group.

8. A photothermographic element comprising a support bearing at least one heat-developable, photosensitive, image-forming photothermographic emulsion layer comprising:
(a) a photosensitive silver halide;
(b) a non-photosensitive, reducible source of silver;
(c) a leuco dye reducing agent; and
(d) a binder;
wherein the leuco dye reducing agent comprises a chromogenic leuco dye compound of the general formula:

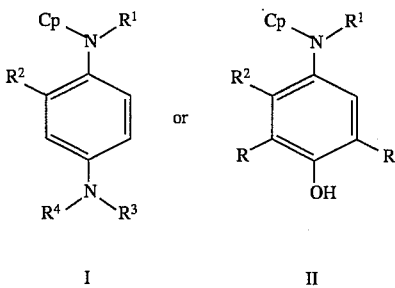

I    II wherein:
(a) R is hydrogen or halogen;
(b) $R^1$ is a C(O)—NH—SO$_2$—$R^5$ group, wherein $R^5$ is a ballasting group;
(c) $R^2$ is a hydrogen atom, an alkoxy group, or an alkyl group;
(d) $R^3$ and $R^4$ are each independently an aliphatic group, an aromatic group, or an -X-Y group, wherein X is an alkylene group containing 1–4 carbon atoms, and Y is a cyano group, a halogen atom, an alkoxy group containing 1–20 carbon atoms, or —OH; and
(e) Cp is a coupler group.

9. The photothermographic element of claim 8 wherein $R^1$ is selected from the group consisting of —C(O)—NH—SO$_2$—C$_6$H$_4$—O—C$_8$H$_{16}$—OH, —C(O)—NH—SO$_2$—C$_6$H$_4$—O—C$_{12}$H$_{25}$, —C(O)—NH—SO$_2$—C$_6$H$_4$—O—C$_{18}$H$_{37}$, —C(O)—NH—SO$_2$—C$_6$H$_4$—O—C$_{22}$H$_{45}$, and —C(O)—NH—SO$_2$—C$_6$H$_4$—O—C(O)—NH—(CH$_2$)$_{36}$—NH—C(O)—OCH$_3$.

10. The photothermographic element of claim 8 wherein $R^2$ is a hydrogen atom, an alkyl group containing 1–20 carbon atoms, or an alkoxy group containing 1–20 carbon atoms.

11. The photothermographic element of claim 10 wherein $R^3$ and $R^4$ are each independently an alkyl group containing 1–20 carbon atoms or an aromatic group containing 5–30 carbon atoms.

12. The photothermographic element of claim 8 wherein $R^3$ and $R^4$ are each independently an alkyl group containing 1–20 carbon atoms or an aromatic group containing 5–30 carbon atoms.

13. The photothermographic element of claim 8 wherein the coupler group is a photographic coupler group.

14. A method of producing an image comprising:
(a) imagewise exposing an element comprising a support bearing at least one heat-developable, photosensitive, image-forming photothermographic emulsion layer comprising:
(i) a photosensitive silver halide;
(ii) a non-photosensitive, reducible source of silver;
(iii) a leuco dye reducing agent; and
(iv) a binder;
wherein the leuco dye reducing agent comprises a chromogenic leuco dye compound of the general formula:

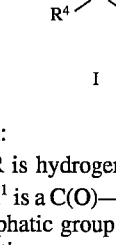

I    II wherein:
(A) R is hydrogen or halogen;
(B) $R^1$ is a C(O)—NH—SO$_2$—$R^5$ group, wherein $R^5$ is an aliphatic group containing 1–50 carbon atoms, an aromatic group containing 5–50 carbon atoms, or a ballasting group;
(C) $R^2$ is a hydrogen atom, an alkoxy group, or an alkyl group;
(D) $R^3$ and $R^4$ are each independently an aliphatic group, an aromatic group, or an -X-Y group, wherein X is an alkylene group containing 1–4 carbon atoms, and Y is a cyano group, a halogen atom, an alkoxy group containing 1–20 carbon atoms, or —OH; and (E) Cp is a coupler group; and (b) heating the element to a sufficient temperature for a sufficient time to develop the image.

15. The method of claim 14 wherein the element is placed in contact with an image-receiving sheet during development and thereafter the image-receiving sheet is stripped from said element.

16. The method of claim 14 wherein $R^1$ is selected from the group consisting of $-C(O)-NH-SO_2-C_6H_4-O-C_8H_{16}-OH$, $-C(O)-NH-SO_2-C_6H_4-O-C_{12}H_{25}$, $-C(O)-NH-SO_2-C_6H_4-O-C_{18}H_{37}$, $-C(O)-NH-SO_2-C_6H_4-O-C_{22}H_{45}$, and $-C(O)-NH-SO_2C_6H_4-O-C(O)-NH-(CH_2)_{36}-NH-C(O)-OCH_3$.

17. The method of claim 14 wherein $R^5$ is an alkyl group containing 1–20 carbon atoms or an aryl group containing 5–30 carbon atoms.

18. The method of claim 14 wherein the coupler group is a photographic coupler group.

* * * * *